US00PP13002P2

(12) United States Plant Patent
Poulsen

(10) Patent No.: US PP13,002 P2
(45) Date of Patent: Sep. 24, 2002

(54) BEGONIA PLANT NAMED 'KENNA'

(75) Inventor: Jens Norgaard Poulsen, Aarhus N. (DK)

(73) Assignee: D.S. Cole Growers, Inc., Loudon, NH (US)

( * ) Notice: Subject to any disclaimer, the term of this patent is extended or adjusted under 35 U.S.C. 154(b) by 19 days.

(21) Appl. No.: 09/654,456

(22) Filed: Aug. 31, 2000

(51) Int. Cl.[7] ..... A01H 5/00

(52) U.S. Cl. ..... Plt./344

(58) Field of Search ..... Plt./344

*Primary Examiner*—Bruce R. Campell
*Assistant Examiner*—Anne Marie Grünberg
(74) *Attorney, Agent, or Firm*—Foley & Lardner

(57) ABSTRACT

A new and distinct cultivar of Begonia plant named 'Kenna' characterized by having larger area of red color on the outer edge of the petals and an inner petal that has deeper yellow color as compared to 'Jutta' grown under the same environmental conditions.

2 Drawing Sheets

BACKGROUND OF THE INVENTION

The present invention relates to a new and distinctive cultivar of Begonia plant, botanically known as *Begonia× hiemalis* and hereinafter referred to by the cultivar name 'Kenna'.

The new cultivar was selected by the inventor, Jens Norgaard Poulsen, in Denmark. The cultivar was discovered by the inventor as a natural sport of the cultivar 'Jutta' (unpatented).

The new cultivar was first asexually propagated by the inventor in Aarhus, Denmark in spring 1999. Subsequent asexual reproduction of the new cultivar by means of tip cuttings has demonstrated that the combination of characteristics as herein disclosed for 'Kenna' are firmly fixed and retained through successive generations of asexual reproduction.

BRIEF DESCRIPTION OF THE INVENTION

The following characteristics distinguish the new cultivar from other Begonia cultivars commercially known and used in the floriculture industry:

1. Larger area of red color on outer edge of petals as compared to 'Jutta'; and
2. Inner petal has deeper yellow color than the petals of 'Jutta'.

'Kenna' has not been observed under all possible environmental conditions. The phenotype of the new cultivar may vary significantly with variations in environment such as temperature, light intensity, and daylength without any change in genotype. Of the many commercial cultivars known to the present inventor, the most similar in comparison to 'Kenna' is the parental cultivar 'Jutta'. In comparison to 'Jutta', 'Kenna' has darker yellow flowers and more red color per petal. 'Kenna' has a larger area of red per petal than 'Jutta' and 'Kenna's' yellow is a richer yellow with orange tones than 'Jutta'.

BRIEF DESCRIPTION OF THE DRAWINGS

The accompanying color photographs of a specimen of 'Kenna' were grown under commercial greenhouse conditions in Loudon, N.H. The characteristics shown are as accurate as possible with photographic illustrations of this type.

The first drawing is a side view of the whole plant.

The second drawing is a close-up of a flower.

DETAILED BOTANICAL DESCRIPTION

The following observations, measurements, and values describe plants grown in Loudon, N.H. under greenhouse conditions which approximate those generally used in commercial practice. Color references are made to The Royal Horticultural Society (R.H.S.) Colour Chart except where general terms of ordinary dictionary significance are used. The phenotype of 'Kenna' has not been observed under all possible environmental conditions. The phenotype of the new cultivar may vary significantly with variations in environment such as temperature, light intensity, day length and humidity, without, however, any change in genotype.

Classification:
- *Botanical.*—A hybrid of the genus *Begonia×hiemalis.*
- *Commercial.*—Begonia c.v. 'Kenna'.

Propagation:
- *Type cutting.*—Tip cuttings.
- *Time to root.*—21–25 days at 21° C. in summer and 17–21 days at 21° C. in winter.
- *Rooting habit.*—Root system is strong and develops rapidly; roots are prolific, dense, fine and fibrous in texture.

Growing conditions:
- *Temperatures.*—21° C. in summer and winter.
- *Photoperiodic treatments.*—10–14 days of short day treatments approximately 6–8 weeks after sticking.
- *Growth retardation.*—Occasional cycocel foliar application.

Plant description: The following description is based on observations taken on 4-month-old plants grown in 15-cm pots.
- *Form.*—Upright.
- *Height.*—25 cm when grown in a 15-cm pot.
- *Width.*—25 cm.
- *Branching.*—Well branching, regardless whether or not pinched; branching as good or better than 'Jutta'.
- *Growth habit.*—Quite vigorous.

Foliage:

*Mature leaf color.*—Upper surface: RHS 139 A. Lower surface: RHS 183 B, veins RHS 147 C.

*Immature leaf color.*—Upper surface: RHS 147 A. Lower surface: Leaf edges RHS 183 D, inner surface and veins RHS 148 C.

*Veination.*—Palmate, smooth on upper, raised on underside.

*Shape.*—Cordate.

*Size.*—8–14 cm in length and 10 cm in width.

*Margin.*—Serrate.

*Tip.*—Acute.

*Texture.*—Upper side is smooth, leathery and glabrous; underside is leathery and sparsely pubescent.

Flowering description:

*Habit.*—Raceme arrangement.

*Natural flowering season.*—Plants flower year round with warm nights.

*Bud shape.*—Ovoid.

Flower:

*Pistil.*—Yes.

*Stamen.*—Yes.

*Quantity.*—Average 3–5 flowers per stem.

*Shape.*—Circular.

*Size.*—Approximately 2.5–4.5 cm in diameter and 1.5 cm in depth.

Petals:

*Number.*—8–20.

*Size.*—1.5–2 cm in length and 1.5–2 cm in width.

*Margin.*—Entire.

*Color and quantity.*—Outer petals: Quantity: 2. Upper surface: 90% yellow RHS 13 B, 10% red coloration on outer edge of petals RHS 34 A. Lower surface: 90% yellow RHS 12 C, 10% red red coloration on outer edge of petals RHS 34 A. Inner petal: Quantity: 6–8. Upper surface: 90% yellow RHS 13 B, 10% red red coloration on outer edge of petals RHS 34 A. Lower surface: 90% yellow RHS 12 C, 10% red red coloration on outer edge of petals RHS 34 A.

Sepals: 2 sepals, oval shaped, RHS 145 A.

Peduncle: Smooth in texture, RHS 145 B.

Petiole: Slightly pubescent, RHS 152 B.

Flower longevity: 2–3 weeks for individual flowers.

Fruit/seed: None produced.

Pistils/stamen: None.

Resistance to pests and disease: 'Kenna' exhibits better resistance to powdery and downy mildew than most *Begonias×hiemalis.*

General observations: 'Kenna' has the general growth habit of the Ilona or Netja group of Begonias. 'Kenna' will typically grow 5% taller than Ilona or Netja types. 'Kenna' is similar to Ilona or Netja types in that it branches well regardless whether or not it is pinched. 'Kenna' has a unique color which is more rich and deep color in comparison to 'Jutta'. The plant is self-cleaning.

I claim:

1. A new and distinct cultivar of Begonia plant named 'Kenna', as described and illustrated.

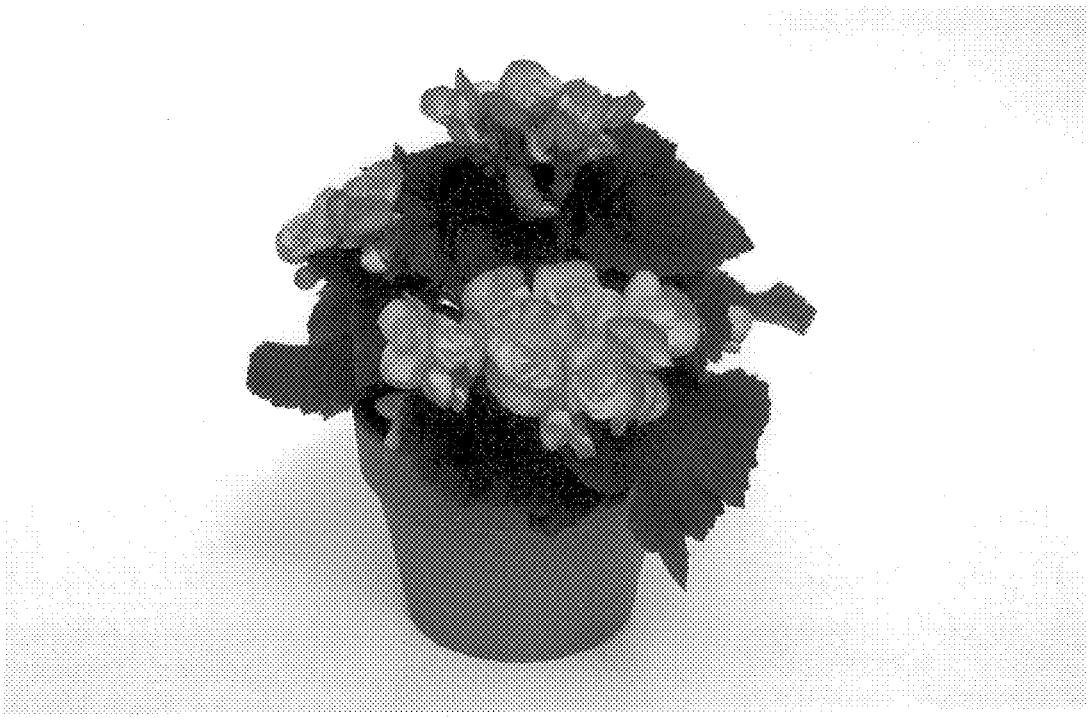

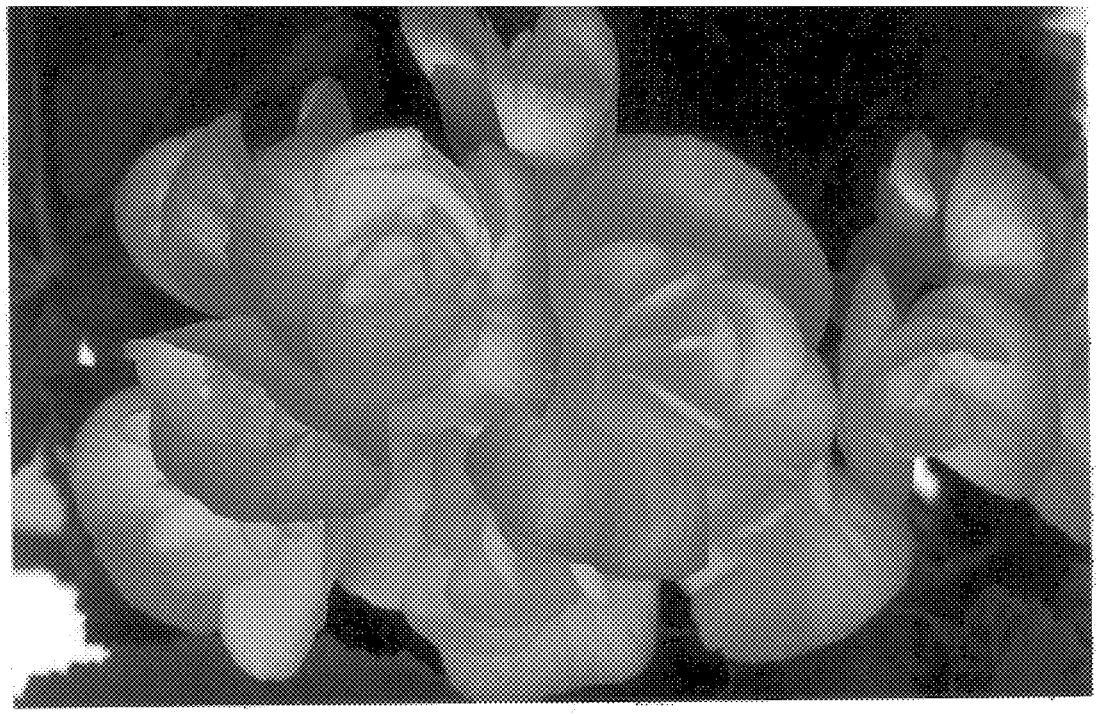

* * * * *